(12) United States Patent
Stork et al.

(10) Patent No.: US 7,615,265 B2
(45) Date of Patent: Nov. 10, 2009

(54) INKJET PRINTING RECORDING MATERIAL

(75) Inventors: Gerhard Stork, Flensburg (DE); Makato Kato, Flensburg (DE); Karsten Lerius, Munkbrarup (DE)

(73) Assignee: Mitsubishi Hitec Paper Flensburg GmbH, Flensburg (DE)

(*) Notice: Subject to any disclaimer, the term of this patent is extended or adjusted under 35 U.S.C. 154(b) by 173 days.

(21) Appl. No.: 10/487,621

(22) PCT Filed: Aug. 22, 2002

(86) PCT No.: PCT/EP02/09391

§ 371 (c)(1), (2), (4) Date: May 7, 2004

(87) PCT Pub. No.: WO03/018324

PCT Pub. Date: Mar. 6, 2003

(65) Prior Publication Data

US 2004/0189778 A1    Sep. 30, 2004

(30) Foreign Application Priority Data

Aug. 24, 2001  (DE) ............................... 101 40 677

(51) Int. Cl.
*B41M 5/40* (2006.01)

(52) U.S. Cl. .............. 428/32.24; 428/32.25; 428/32.28; 428/32.3; 428/32.35

(58) Field of Classification Search .............. 428/32.24, 428/32.25, 32.3, 32.35, 32.28
See application file for complete search history.

(56) References Cited

U.S. PATENT DOCUMENTS

| 3,391,090 | A | * | 7/1968 | Schiegg ....................... 528/405 |
| 4,740,420 | A | | 4/1988 | Akutsu et al. |
| 5,660,622 | A | * | 8/1997 | Nikoloff ................. 106/287.34 |

FOREIGN PATENT DOCUMENTS

| CN | 2411892 | | 12/2000 |
| DE | 24 01 866 | A1 | 7/1975 |
| DE | 25 33 957 | A1 | 2/1977 |
| DE | 34 33 528 | C2 | 4/1985 |
| DE | 100 54 219 | A1 | 5/2002 |
| EP | 0 602 326 | A1 | 6/1994 |
| EP | 0 914 962 | A2 * | 5/1999 |
| EP | 0947 350 | A1 * | 10/1999 |
| EP | 1 016 545 | A1 | 7/2000 |
| EP | 1 029 703 | A1 | 8/2000 |
| GB | 1486852 | | 7/1975 |
| JP | 09099630 | A | 4/1997 |
| JP | 09240139 | | 9/1997 |
| JP | 10152544 | | 6/1998 |
| JP | 11277887 | | 10/1999 |
| JP | 11277888 | | 10/1999 |
| JP | 11291622 | | 10/1999 |
| WO | WO 01/53070 | A1 | 7/2001 |

OTHER PUBLICATIONS

Translation of Chinese Office Action dated Oct. 2, 2006 issued for Patent Application No. 02816617.5.

* cited by examiner

*Primary Examiner*—Betelhem Shewareged
(74) *Attorney, Agent, or Firm*—Cohen Pontani Lieberman & Pavane LLP

(57) ABSTRACT

A novel recording material for the inkjet printing process has a substrate and an ink receiving layer which is applied on at least one side of the substrate, the ink receiving layer containing an inorganic pigment and an ink fixative comprising at least two substances. The first substance is a polyamine epichorohydrin and the second substance is a polyvalent metal salt. This recording material is characterized in that the first substance is a medium-molecular, branched polyamine epichlorohydrin condensation product, the ratio of the first substance to the second substance is between 3:1 and 16:1, the pigment makes up at least 80 percent by weight with a $D_{50}$ particle size (Malvern) ranging from 4 μm inclusive to 12 μm inclusive, and the ratio of ink fixative to pigment ranges from 1:2 inclusive to 1:6 inclusive. The invention is further directed to a method for recording by the discontinuous inkjet printing process which uses the novel recording material.

10 Claims, No Drawings

INKJET PRINTING RECORDING MATERIAL

PRIORITY CLAIM

This is a U.S. national stage of application No. PCT/EP02/09391, filed on 22 Aug. 2002. Priority is claimed on that application and on the following application(s): Country: Germany, Application No.: 101 40 677.0, Filed: 24 Aug. 2001.

BACKGROUND OF THE INVENTION

1. Field of the Invention

The present invention is directed to a recording material for the inkjet printing process having a substrate and an ink receiving layer which is applied on at least one side of the substrate, the ink receiving layer containing an inorganic pigment and an ink fixative comprising at least two substances, the first substance being a polyamine epichlorohydrin and the second substance being a polyvalent metal salt. The invention is further directed to a process for recording by discontinuous inkjet printing which uses the novel recording material.

2. Description of the Prior Art

Reaction products which are produced on the basis of amine compounds and epihalohydrins as auxiliaries for the ink receiving layers of inkjet recording materials are known. In order to improve the water fastness of printed images which are generated by means of inkjet printers and which should be distinguished by excellent printing quality, JP-A-11 277 888, for example, proposes an auxiliary with a linear cationic resin that is formed as reaction product of an amine component containing a secondary amine and another amine component containing at least two amino groups and an epihalohydrin.

JP-A-11 277 887 is likewise directed to an auxiliary which increases water fastness and which has a structural formula of the linear cationic resin that is different than that in the above-cited reference and has a comparable effect. According to the description, however, this structural formula is expanded in order to reduce ink bleeding in images printed by inkjet printers. In both of the references cited above, the indicated viscosity of the respective 20-percent aqueous solutions containing the proposed auxiliary is between 50 and 500 m Pa*s (B-type; 30° C.).

JP-A-10 152 544 has the object of providing an inkjet recording paper which allows only slight ink bleeding in printed images generated by aqueous inks and, beyond this, enables a high color concentration and excellent water fastness of the printed images. This object is supposed to be met through an addition to the coating compound in the form of a branched cationic resin presenting a reaction product of ammonia and at least one, preferably primary, secondary or tertiary amine and an epihalohydrin. Further, preferable amines are polyalkylene polyamine and alkanolamine. The Brookfield viscosity of the 10-percent aqueous solution of this cationic resin is 1 to 30 m Pa*s (60 rpm/25° C.).

With the aim of providing a production process for inkjet recording papers which has only low bleeding of ink droplets of aqueous ink and which enables printed images with high color density and excellent water fastness, JP-A-09 240 139 proposes application of a branched cationic resin which is formed as reaction product of a polyalkylene polyamine and an epihalohydrin and further, as the case may be, with an aliphatic amine component. The Brookfield viscosity of a 10-percent aqueous solution containing the proposed cationic resin is indicated as 30 m Pa*s (60 rpm/25).

The teaching to be gathered from the texts cited above is the suitable selection of the cationic resins to be used as auxiliaries in medium-molecular linear form or low-molecular branched form. However, these texts do not indicate possible quantity ratios of the cationic resins to the pigments present in the ink receiving layers, nor do they indicate that it is advantageous to combine the cationic resins to be used as auxiliaries with metal salts to obtain improved characteristics for recording materials to be used in inkjet printing methods.

A polyamide polyamine epichlorohydrin as ink fixative in the ink receiving layer of an inkjet recording material is known from JP-A-09 099 630. However, neither its precise structure nor its molecular weight is disclosed. Amorphous silicon dioxide is proposed as pigment; its particle size is indicated only in a very general way as averaging in the range of 6 to 13 μm.

According to EP-A-0 914 962, outstanding inkjet recording characteristics and superior printability in offset printing are achieved in a recording material due to its surface being especially well bonded; further, this recording material is distinguished by a high degree of water fastness. It is stated in this text that this goal is achieved by a linear cationic resin in the ink receiving layer. Dimethylamine epichlorohydrin polycondensation products, among others, are mentioned as examples of this cationic resin. In addition to the cationic resin, the ink receiving layer further contains binders and, as the case may be, pigments. The text does not indicate any advantageous characteristics of the pigments in the ink receiving layer. Also, the description in this text does not disclose any teaching regarding the mixture ratio of ink fixative to pigment. A ratio of 1:10 is disclosed by way of example, while other examples disclose pigment-free ink receiving layers.

Finally, EP-A-0 602 326 discloses a quaternary salt of a linear dimethylamine epichlorohydrin adduct with a degree of polymerization between 2 and 2000 as ink fixative in the recording layer of an inkjet recording paper. In addition to improved ink fixing, color distortion is prevented in the applied printed images through combination with a (meth) acrylamide diallylamine copolymer. Insofar as they are used at all in the recording layers disclosed in this text, inorganic and organic pigments considered to be suitable are those having a particle size in the range of 4 μm. There is no indication in the text about the advantageous combination of the dimethylamine epichlorohydrin adduct with polyvalent metal salts as ink fixative.

Also, the use of divalent or polyvalent metal salts in the recording layer of inkjet recording materials is known and is proposed without combining with other agents improving ink fixing in DE-A-25 33 957 and DE-A-24 01 866, for example. However, using metal salts alone or predominantly as ink fixatives in inkjet recording layers has the fundamental disadvantage that a true-color reproduction of applied ink print images is rarely achieved.

EP-A-1 01 016 545 discloses a recording material for inkjet printing in which a mat finish, greater ink absorption, image quality, water-tightness, light fastness and ink transfer, as well as resistance to ink bleeding, are to be achieved by means of a binder mixture for the image receiving layer containing polyethylene glycol and polyvinyl alcohol in a defined ratio. The image receiving layer can contain polyvalent metal salts and a compound from the group of polymeric quaternary ammonium compounds or base polymers such as poly(dimethylaminoethyl) methacrylate, polyalkylene polyamine and condensation products thereof with dicyanodiamide and amino-epichlorohydrin polycondensates. The structure and molecular weight of these compounds are not disclosed. For the purpose of increasing the density of open porous structures, the image receiving layer contains colloidal oxides such as colloidal silicon dioxide or silicon dioxide modified with aluminum oxide without disclosing advantageous quantity ratios.

Finally, DE 34 33 528 C2 proposes a recording material for inkjet printing with a carrier containing, at least in the surface region, a water-soluble metal salt of a metal with an ionic valence of 2 to 4 and a cationic organic material chosen from alkylamine salts, quaternary ammonium salts, polyamines and basic latices from the group of polyamine latices and alkylammonium latices. Examples of polyamines mentioned therein include polyethylamine epichlorohydrin. However, the text does not contain further indications of its especially suitable representatives nor does it refer to any particular arrangements of specific representatives of polyethylamine epichlorohydrin. The text also does not indicate any teaching of advantageous characteristics of the pigments to be employed, e.g., with respect to particle size.

For a long time, pigment-based recording inks were rarely used in place of inks based on organic dyes, particularly acidic azo dyes. Problems with this type of recording ink have to do with the low light fastness of the organic dyes along with the problem of fading and discoloration of the printed images, which could be solved heretofore only unsatisfactorily by means of UV absorbers in the recording inks and by means of color stabilizers in the inkjet recording materials. The pigment-based recording inks that have been used in the meantime have substantially greater light stability than the organic dye-based inks mentioned above. However, the pigment-based recording inks have the problem of ink bleeding, by which is meant that directly adjoining printed patterns of different colors run into one another directly after the printing process. The recording material according to the invention was developed for use with pigment-based recording inks and significantly reduces the problem of ink bleeding.

There are basically two different processes of droplet generation in inkjet printing. The continuous process provides an inkjet which is ejected under pressure from a nozzle and which separates into very small droplets at a certain distance from the nozzle due to surface tension. The droplets are electrically charged and, by means of deflecting plates which are electronically controlled by the electrical field, are subsequently either deflected into a collecting vessel or placed on the recording material depending on the printed image to be generated.

In the discontinuous drop-on-demand process, as it is called, the ink droplets, depending on the printed image to be generated, are generated and ejected from a nozzle only when an image point is to be generated on the recording material. One type of drop-on-demand printer uses the piezoelectric effect in which an electrically controlled piezo-element separates an ink droplet from the reservoir of recording ink and ejects this droplet from a nozzle. In contrast, bubblejet printers use an electrically controlled heating element which allows very small quantities of aqueous ink to form in a steam bubble. The resulting steam pressure ejects the droplet.

SUMMARY OF THE INVENTION

The invention is directed to recording materials which can be used in both discontinuous processes.

It is the object of the present invention to provide an economical recording material for inkjet printing processes which is particularly suitable for printing upon with pigment-based recording inks in discontinuous processes. The novel recording material ensures outstanding fixing of the applied inks and thus reduces ink bleeding. The orientation of the novel recording material toward pigmented inks enables an extensive light fastness of the applied printed images.

Since pigmented inks are preferably used in poster printing and since the posters produced in this way, e.g., advertising posters, are exposed to direct sunlight, a novel recording material characterized by high stability with respect to any tendency toward yellowing is preferably provided. The recording material should also ensure that the applied printed images exhibit at least acceptable resistance to smudging when wet.

In contrast to the teachings previously disclosed in this technical field, the inventors recognized as the result of numerous production tests and comparison tests that the above-stated object is met by a recording material for the inkjet printing process with a substrate and an ink receiving layer which is applied on at least one side of the substrate, the ink receiving layer comprising an inorganic pigment and an ink fixative which includes at least two substances, the first substance being a polyamine epichlorohydrin and the second substance being a polyvalent metal salt, wherein the first substance is a medium-molecular, branched polyamine epichlorohydrin condensation product; the ratio of the first substance to the second substance is between 3:1 and 16:1; the pigment makes up at least 80 percent by weight with a $D_{50}$ particle size (Malvem) ranging from 4 µm inclusive to 12 µm inclusive; and the ratio of ink fixative to pigment ranges from 1:2 inclusive to 1:6 inclusive.

Within the meaning of the present invention, the polyamine epichlorohydrin condensation product is defined as medium-molecular insofar as it has a viscosity in a range from 15 m Pa*s to 50 m Pa*s as a 10-percent aqueous solution. The above-mentioned viscosity is determined using Brookfield (spindle 1 at 100 rpm and 25° C.).

The invention is based on the choice of the polyamine epichlorohydrin condensation product as first substance of the ink fixative containing at least two substances. It is essential to the invention that the polyamine epichlorohydrin condensation product is in medium-molecular, branched form. Other configuration types of polyamine epichlorohydrin condensation product prove to be unsuitable for various reasons; for example, the use of a low-molecular, non-branched polyamine epichlorohydrin condensation product is to be avoided because recording materials containing them have too strong an odor due to the free amine.

As second substance, the ink fixative must comprise a polyvalent metal salt in order to meet the object upon which the invention is based.

Based on comparisons carried out in the framework of extensive series of tests, the inventors recognized that good ink fixing with minimum ink bleeding behavior and acceptable resistance to smudging when wet occurs only with a ratio (oven dry) of the first substance to the second substance of between 3:1 and 16:1. A preferable ratio (oven dry) of the first substance to the second substance is in the range between 6:1 and 14:1 with excellent ink fixing and greatly reduced ink bleeding behavior accompanied by particularly convincing resistance to smudging when wet.

The second substance of the ink fixative is particularly magnesium chloride, aluminum chloride and particularly preferably calcium chloride as representatives of the polyvalent metal salts.

The ratio, according to the invention, of ink fixative to pigment ranges from 1:2 to 1:6 with respect to the percentage by weight of pigment and ink fixative in the ink receiving layer. This ratio is limited on the one hand by sharply decreasing resistance to wet smudging which is not acceptable in larger amounts of ink fixative beyond an ink fixative-to-pigment ratio of 1:2 and, on the other hand, by an increasingly worsening ink bleeding behavior which is no longer convincing in smaller quantities of ink fixative beyond an ink fixative-to-pigment ratio of 1:6.

In accordance with the findings of the series of tests upon which the present invention is based, the inventors recognized that particularly good characteristics of the novel recording material result when the ink fixative-to-pigment ratio ranges from 1:3 inclusive to 1:5.5 inclusive with respect to the percentage by weight of pigment and ink fixative in the ink receiving layer; the percentage by weight again refers to all of the ink fixative and pigment incorporated in the ink fixative layer.

However, it was completely surprising to the inventors that the object upon which the present invention is based could be fully and convincingly met when, simultaneous with the above-mentioned features, the inorganic pigment makes up at least 80 percent by weight with a particle size ranging from 4 µm inclusive to 12 µm inclusive and, in a particularly advantageous manner, from 5 µm to 12 µm inclusive as $D_{50}$ value (Malvern—that is, determined in accordance with the specifications of the pigment producer using the Malvern method). A range between 6 µm and 12 µm as $D_{50}$ value (Malvern) is particularly preferred.

It has been shown in comparison tests that the ink bleeding behavior is significantly worse when poly-diallyldimethylammonium chloride (poly-DADMAC) is used as ink fixative alone or exclusively combined with polyvalent metal salt. The use of polyethylene amine or poly-dicyanodiamide is excluded due to an increased tendency toward yellowing in the recording materials having these cationic polymers.

According to the invention, the ink fixative of the recording material according to the invention comprises the polyamine epichlorohydrin condensation product to be used as first substance and the second substance comprising a polyvalent metal salt. However, the ink fixative can also contain one or more additional compounds conventional for ink fixative such as poly-diallyldimethylammonium chloride, cationic polyacrylamides, cationic polyacrylates, polyvinylamines, polyethyleneimines and polydicyanodiamides or a low-molecular, non-branched polyamine epichlorohydrin condensation product insofar as it makes up an amount not exceeding 30 percent by weight, particularly 10 percent by weight, with respect to the total quantity of ink fixative.

It has proven advantageous that the proportion by weight of ink fixative in the ink receiving layer preferably ranges from 5 percent by weight to 20 percent by weight; this total proportion can be selected tending toward the lower limit when applying ink receiving layers with high mass per unit area within the above range.

The proportion of pigment in the ink receiving layer of the recording material according to the invention ranges from 30 to 70 percent by weight. For this purpose, aluminum hydroxide, silica gel and silicic acid have proven successful in particular. The last three pigments can be modified by aluminum or aluminum oxide, or not modified.

The inorganic pigments mentioned previously can make up the pigment proportion of the ink receiving layer of the recording material, according to the invention, individually or in combination with one another and/or in combination with other inorganic pigments.

The ink receiving layer of the recording material according to the invention comprises a proportion of binder and co-binder ranging from 10 to 55 percent by weight. Aqueous polymer dispersions of ethylene-vinyl acetate and particularly styrene-butadiene latex, polyacrylates and solutions of partially or completely saponified polyvinyl alcohol used alone or in combination have proven particularly favorable.

Aside from the ingredients discussed above, the ink receiving layer of the recording material according to the invention can also contain additional components such as caustic soda, optical brightening agents and defoaming agents without being limited thereto. They are added as needed and constitute up to 5 percent by weight of the ink receiving layer, the individual proportions taken together accounting for 100 percent by weight.

In order to satisfy the spectrum of requirements in a convincing manner, the selected mass per unit area of the ink receiving layer should not be too small because otherwise the resistance to smudging when wet decreases too sharply and ink bleeding cannot be reduced to a sufficient degree. The mass per unit area of the ink receiving layer is limited at the top primarily for economical reasons.

It has been shown in numerous tests that it is advantageous to form the ink receiving layer in two layers positioned one on top of the other. According to a preferred embodiment, a bottom layer communicates with the substrate or with a preparation layer applied to the substrate, and a top layer is applied to the bottom layer. Especially good results can be achieved when the first layer has a mass per unit area between 4 and 12 $g/m^2$, preferably between 6 and 8 $g/m^2$, and the second layer has a mass per unit area between 2 and 10 $g/m^2$, preferably between 4 and 6 $g/m^2$. The same teachings apply for both layers with respect to the selection of components substantial to the invention and the ratio of these components relative to one another, particularly also in their preferred embodiment forms. The two layers also have the same auxiliary components corresponding to the disclosures indicated herein.

When the ink receiving layer is formed with only one layer, the recommended mass per unit area of this layer is between 4 and 18 $g/m^2$, particularly ranging from 5 to 10 $g/m^2$ and especially particularly from 7 to 9 $g/m^2$.

The solids contents and viscosities of the coating compounds for forming an individual layer or, in the preferred embodiment form, two layers of the ink receiving layer according to the invention are adapted to the coating method to be used.

In principle, the invention is not limited with respect to the coating mechanisms that are used for applying the ink receiving layer. Leveling or equalizing coating methods such as doctor rolls or blades and contour coating methods such as nozzle coaters or preferably curtain coaters and air brushes are possible in particular, although the invention is not limited thereto. If the ink receiving layer is applied in two layers, it is particularly advantageous to apply the first layer with a leveling coating method such as doctor rolls or blades—in the preferred embodiment form, on-line inside the paper machine—and to apply the second layer with a contour coating method, preferably with a curtain coater or an air brush which can be integrated inside a separate coating machine.

At least one preparation layer preferably having a mass per unit area ranging from 0.5 to 2 $g/m^2$ is preferably arranged between the substrate and the individual layer, or first layer in the preferred embodiment form, of the ink receiving layer. The preparation layer can be formed as a single starch coat.

In a particularly preferred embodiment form, the recording material according to the invention comprises a back coating on the side located opposite from the side with the ink receiving layer; this back coating can be formed as an ink receiving layer or as a single starch coat. As a starch coat, it serves to ensure good grip so that there will be no transporting problems in the inkjet printers. Improved printability can also be achieved particularly in offset printing processes by means of a single starch coat. The starch coat formed as a back coating preferably has a mass per unit area ranging from 0.1 to 2.0 g/m².

The invention further comprises a method for recording using the discontinuous inkjet printing process with a pigment-based recording ink and with a recording material according to the invention which can be formed in one of the preferred embodiment forms described above. In the novel method, the recording material according to the invention can be printed upon by drop-on-demand printers which use either the piezoelectric effect or which, as bubblejet printers, use an electrically controlled heating element to eject very small ink droplets.

The values specified in the description and patent claims for mass per unit area, percent by weight, parts by weight and component ratios refer to O.D. weight, i.e., oven-dry parts by weight, unless otherwise noted. The abbreviation "A.D." stands for air dry and, when used, means that the components thus characterized are described in their commercially available as -shipped form.

The following examples and comparison examples will illustrate the invention more fully.

DETAILED DESCRIPTION OF THE PREFERRED EMBODIMENTS

Production of a Substrate

A paper web of bleached, milled hardwood and softwood kraft pulps is produced as a substrate on a fourdrinier paper machine with the addition of the usual quantities of conventional additives with a mass per unit area of 82 g/m². A starch preparation of 0.8 g/m² is applied to the front side of the paper web and a starch preparation of 0.4 g/m² is applied to the back of the paper web.

Basic Recipe 1 for the Production of Coating Compounds for an Ink Receiving Layer for Examples 1, 5, 6 and 7 According to the Invention and Comparison Examples 2, 3, 4, 8 and 9

The following components referring to a total of 500 parts per weight (A.D.) are added to a vessel accompanied by continuous stirring:

As ink fixative in the coating compound in Example 1, a composition of medium-molecular, branched polyamine epichlorohydrin condensation product and calcium chloride is used in a ratio of polyamine epichlorohydrin condensation product to calcium chloride of 9.8:1.

In contrast to Example 1, the coating compound according to Comparison Example 2, with all other components remaining the same, has poly-diallyldimethylammonium chloride instead of polyamine epichlorohydrin condensation product. To form the single-layer ink receiving layers, the coating compounds are applied at 8.5 g/m² to the front side of the paper web whose production was described above. Samples of Example 1 and Comparison Example 2 were made in this way.

Using an inkjet printer, HP DesignJet 2500 CP by Hewlett Packard, and UV inks by the same manufacturer, a control printing is applied to both samples in order to analyze the ink bleeding behavior (printing mode: normal, no color matching; printer driver: heavy coated paper). Based on visual inspection, the ink bleeding behavior of the samples of Example 1 is judged to be good, while the ink bleeding behavior of the samples of Comparison 2 is judged to be poor.

For the following Examples 5, 6 and 7 and Comparison Example 3, 4, 8 and 9, coating compounds are produced according to the oven dry proportions in Example 1 and, corresponding to Example 1, are applied to a paper web, whose production was described above, with a mass per unit area according to Table 1. Compared to Example 1, the ratio of the medium-molecular branched polyamine epichlorohydrin condensation product to calcium chloride varies.

Again, using an inkjet printer, HP DesignJet 2500 CP by Hewlett Packard (printing mode: normal, no color matching; printer driver: heavy coated paper), and UV inks by the same manufacturer, a control printing is applied to the samples to analyze the ink bleeding behavior. The ink bleeding behavior of the samples is assessed visually.

In order to analyze the resistance to smudging when wet, the printed images by which the ink bleeding behavior of the samples was judged previously are sprinkled with water. After a waiting period of 2 seconds, a finger is repeatedly rubbed with uniform pressure over the printed image. The printed image should smudge as little as possible, ideally not at all.

| Component | % (O.D.) | Solids Content [%] | % (A.D.) |
|---|---|---|---|
| Water[*4] | — | — | 279.6/278.6/270.4 |
| Caustic soda [10-percent] | 0.3 | 10 | 3.0 |
| Pigment[*1] | 58.8 | 100 | 58.8 |
| Optical brightening agent | 3.0 | 50 | 6.0 |
| Mixture of binder (PVAI[*2], fully saponified) and co-binder (EVAC[*3]) | 24.8 | 20 | 124.0 |
| first substance ink fixative | 11.8 | | |
| Ex. 1: Polyamine epichlorohydrin condensation product-medium-molecular, branched | | 48 | 24.6 |
| Comparison Ex. 2: Poly-DADMAC | | 36 | 32.8 |
| Calcium chloride | 1.2 | 30 | 4.0 |
| Defoaming agent | 0.1 | 10 | 1.0 |
| Total | 100 | 20 | 500 |

[*1] Pigment mixture of two silica gels not modified by aluminum, particle size at 80 percent by weight: 8 μm; at 20 percent by weight: 10 μm; $D_{50}$ value (Malvern)
[*2] Polyvinyl alcohol
[*3] Ethylene vinyl acetate
[*4] Example 1/Example 2/Comparison Example 3

In Table 1, examples according to the invention are indicated by "EB" and comparison examples are indicated by "VB". The determined measurements and findings are given in Table 1:

TABLE 1

| Example | Ratio of amine epichlorohydrin condensation product to calcium chloride | Viscosity of coating compound [Brookfield (spindle 2/50 rpm/25° C.)] | Mass/unit area of ink receiving layer [g/m²] | Ink bleeding behavior | Resistance to smudging when wet |
|---|---|---|---|---|---|
| 3 VB | 1:5 | 744 | 8.4 | good | poor |
| 4 VB | 1.5:1 | >2000 | 7.9 | good | poor |
| 5 EB | 3:1 | 360 | 8.4 | good | satisfactory |
| 6 EB | 9:1 | 336 | 8.2 | good | good |
| 7 EB | 12.5:1 | 352 | 8.2 | good | good |
| 8 VB | 20:1 | 368 | 8.3 | unsatisfactory | good |
| 9 VB | 100:1 (no calcium chloride) | 368 | 8.4 | poor | good |

Basic Recipe 2 for the Production of Coating Compounds for an Ink Receiving Layer for Examples 11, 14, 17 and 20 According to the Invention and Comparison Examples 10, 12, 13, 15, 16, 18, 19 and 21 to 24:

The following components referring to a total of 500 parts per weight (A.D.) are added to a vessel while continuously stirring:

| Component | % (O.D.) | Solids Content [%] | % (A.D.) |
|---|---|---|---|
| Water | — | — | 279.6 |
| Caustic soda [10-percent] | 0.3 | 10 | 3.0 |
| Pigment | 58.8 | 100 | 58.8 |
| Optical brightening agent | 3.0 | 50 | 6.0 |
| Mixture of binder (PVAl*¹, fully saponified) and co-binder (EVAC*²) | 24.8 | 20 | 124.0 |
| Polyamine epichlorohydrin condensation product | 11.8 | 50 | 23.6 |
| Calcium chloride | 1.2 | 30 | 4.0 |
| Defoaming agent | 0.1 | 10 | 1.0 |
| Total | 100 | 20 | 500 |

*¹Polyvinyl alcohol
*²Ethylene vinyl acetate polymer

Silica gel which is not modified by aluminum and has a pore volume of 1.2 ml/g is used as pigment with the following average particle sizes and specific inner surface area:

| | Pigment 1 | Pigment 2 | Pigment 3 | Pigment 4 | Pigment 5 |
|---|---|---|---|---|---|
| Particle size [μm] $D_{50}$ (Malvern) | 4 | 6.5 | 8 | 10 | 15 |
| Specific inner surface [m²/g] | 290 | 390 | 290 | 390 | 175 |

The ink receiving layer provided in the examples for basic recipe 2 is a composition containing as first substance a polyamine epichlorohydrin condensation product with the following difference:

| | | |
|---|---|---|
| Ink fixative A: | medium-molecular, non-branched | (36.5 m Pa * s) |
| Ink fixative B: | medium-molecular, branched | (35 m Pa * s) |
| Ink fixative C: | high-molecular, non-branched | (91 m Pa * s) |

Further, the ink fixative contains calcium chloride as second substance which is used in a ratio of polyamine epichlorohydrin condensation product to calcium chloride of 9.8:1.

The numbers appearing in parentheses in the preceding list of ink fixatives show the viscosity of the polyamine epichlorohydrin condensation product as 10-percent aqueous solution as measured with Brookfield (spindle 1 at 100 rpm and 25° C.)

Examples 11, 14, 17, 20 and Comparison Examples 10, 12, 13, 15, 16, 18, 19 and 21 to 24

Fifteen samples of different recording materials for the inkjet printing process were produced. Fifteen different coating compounds corresponding to the basic recipe given above were prepared. Each of the five pigments 1, 2, 3, 4 and 5 introduced were combined with each of the ink fixatives A, B or C together with calcium chloride. The coating compounds were applied to the paper web, whose production was described above, to form the ink receiving layers. Again, using an inkjet printer, HP DesignJet 2500 CP by Hewlett Packard (printing mode: normal, no color matching; printer driver: heavy coated paper), and UV inks by the same manufacturer, a control printing is applied to the 20 samples to examine the ink bleeding behavior. The ink bleeding behavior of the samples is assessed visually.

In Table 2, examples according to the invention are indicated by "EB" and comparison examples are indicated by "VB". The determined measurements and findings are given in Table 2:

TABLE 2

| Example | Pigment | Ink fixative | Viscosity of coating compound [Brookfield (spindle 2/50 rpm/25° C.)] | Mass/unit area of ink receiving layer [g/m²] | Ink bleeding behavior |
| --- | --- | --- | --- | --- | --- |
| 10 VB | 1 | A | >800 | 8.4 | poor |
| 11 EB | 1 | B | 536 | 8.2 | barely good |
| 12 VB | 1 | C | >800 | 8.6 | poor |
| 13 VB | 2 | A | 408 | 7.8 | poor |
| 14 EB | 2 | B | 344 | 8.8 | good |
| 15 VB | 2 | C | >800 | 8.7 | poor |
| 16 VB | 3 | A | 352 | 7.8 | unsatisfactory |
| 17 EB | 3 | B | 264 | 8.3 | good |
| 18 VB | 3 | C | >800 | 8.8 | poor |
| 19 VB | 4 | A | 672 | 8.0 | poor |
| 20 EB | 4 | B | 440 | 8.1 | good |
| 21 VB | 4 | C | >800 | 8.1 | poor |
| 22 VB | 5 | A | 208 | 8.3 | very poor |
| 23 VB | 5 | B | 144 | 8.0 | poor |
| 24 VB | 5 | C | 720 | 8.1 | poor |

Based on the basic recipe 2 and the ink receiving layer components according to Example 17, the ink fixative-to-pigment ratio varies. The samples produced in this way are analyzed with respect to ink bleeding behavior and resistance to smudging when wet of the printed images applied to them.

In order to analyze the resistance to smudging when wet, the printed images which were previously used for judging the ink bleeding behavior of the samples were sprinkled with water. After a waiting period of 2 seconds, a finger is repeatedly rubbed with uniform pressure over the printed image. The printed image should smudge as little as possible, ideally not at all.

Examples 17, 26, 27 and Comparison Examples 25, 28

For Comparison Example 25 and Example 26 according to the invention, a smaller amount of ink fixative and, therefore, a greater amount of all other components are added to a vessel while continuously stirring in order to reduce the proportion of ink fixative—referring to 500 parts per weight (A.D.) of the basic recipe 2. For Example 27 according to the invention and Comparison Example 28, a greater amount of ink fixative and, therefore, a smaller amount of all other components are added to a vessel while continuously stirring in order to increase the proportion of ink fixative referring to 500 parts per weight (A.D.) of basic recipe 2. The subsequent production of the samples and the respective application of a control print are carried out in accordance with the preceding description.

Table 3 shows the adjusted ink fixative-to-pigment ratios and the visually assessed ink bleeding behavior of the samples and the resistance to smudging when wet of the applied printed images. Examples according to the invention are indicated by "EB" and comparison examples are indicated by "VB".

TABLE 3

| Example | Ink fixative-to-pigment ratios | Ink bleeding behavior | Resistance to smudging when wet |
| --- | --- | --- | --- |
| 25 VB | 1:10 | poor | very good |
| 26 VB | 1:5 | good | good |

TABLE 3-continued

| Example | Ink fixative-to-pigment ratios | Ink bleeding behavior | Resistance to smudging when wet |
| --- | --- | --- | --- |
| 17 EB (see also TABLE 2) | 1:4.53 | good | good |
| 27 EB | 1:3.3 | good | satisfactory |
| 28 VB | 1:1.5 | good | poor |

The examples according to the invention illustrate particularly clearly that the recording material according to the invention convincingly succeeds in providing an economical recording material for inkjet printing processes that ensures excellent fixing of the applied inks particularly when printing with pigment-based recording inks and accordingly reduces ink bleeding, which is not the case in the comparison examples. Further, the examples according to the invention show that the novel recording material ensures an acceptable resistance to smudging when wet in the applied printed images, which the comparison examples are not capable of providing.

What is claimed is:

1. A recording material for an inkjet printing process comprising a substrate and an ink receiving layer applied on at least one side of the substrate, the ink receiving layer containing an inorganic pigment and an ink fixative comprising at least first and second substances, the first substance being a polyamine epichlorohydrin and the second substance being a polyvalent metal salt, wherein the first substance is a branched polyamine epichlorohydrin condensation product that has a viscosity in a range from 15 m Pa*s to 50 m Pa*s as a 10-percent aqueous solution as determined by using a Brookfield spindle 1 at 100 rpm and 25° C., the ratio of the first substance to the second substance is between 3:1 and 16:1, at least 80 percent by weight of the pigment is made of particles having a $D_{50}$ particle size (Malvern) ranging from 4 μm inclusive to 12 μm inclusive, and the ratio of ink fixative to pigment ranges from 1:2 inclusive to 1:6 inclusive.

2. The recording material of claim 1, wherein the second substance is a polyvalent metal salt selected from a group including magnesium chloride, aluminum chloride and calcium chloride.

3. The recording material of claim 1, characterized in that the ratio of the first substance to the second substance is between 6:1 and 14:1.

4. The recording material of claim 1, wherein at least 80 percent by weight of the pigment is made of particles with a $D_{50}$ particle size (Malvern) ranging from 6 μm to 12 μm.

5. The recording material of claim 1, wherein the pigment is selected from the group including aluminum hydroxide, silicic acid and silica gel.

6. The recording material of claim 1, wherein the ratio of ink fixative to pigment ranges from 1:3 inclusive to 1:5.5 inclusive.

7. The recording material of claim 1, wherein the ink receiving layer includes at least one binder selected from the group including polyvinyl alcohol, styrene-butadiene latex, polyacrylates and polymer dispersions of ethylene-vinyl acetate.

8. The recording material of claim 1, further comprising at least one preparation layer arranged between the substrate and the ink receiving layer.

9. The recording material of claim 1, wherein the ink receiving layer includes two layers positioned one on top of the other.

10. A method for recording using a discontinuous inkjet printing process comprising the step of applying a pigment-based recording ink using a discontinuous inkjet printing process onto a recording material according to claim 1.

* * * * *